United States Patent
Erickson

(10) Patent No.: US 6,419,705 B1
(45) Date of Patent: Jul. 16, 2002

(54) EXPANDABLE FUSION DEVICE AND METHOD

(75) Inventor: Richard A. Erickson, Edina, MN (US)

(73) Assignee: Sulzer Spine-Tech Inc., Minneapolis, MN (US)

(*) Notice: Subject to any disclaimer, the term of this patent is extended or adjusted under 35 U.S.C. 154(b) by 0 days.

(21) Appl. No.: 09/338,688

(22) Filed: Jun. 23, 1999

(51) Int. Cl.[7] .................................................. A61F 2/44
(52) U.S. Cl. ................................ 623/17.16; 623/17.15; 623/17.11
(58) Field of Search ......................... 623/17.11, 17.12, 623/17.13, 17.14, 17.15, 17.16, 17.4

(56) References Cited

U.S. PATENT DOCUMENTS

| | | | |
|---|---|---|---|
| 4,309,777 A | * | 1/1982 | Patil ........................... 3/1.91 |
| 4,401,112 A | | 8/1983 | Rezaian |
| 4,501,269 A | | 2/1985 | Bagby |
| 4,554,914 A | | 11/1985 | Kapp et al. |
| 4,657,550 A | | 4/1987 | Daher |
| 4,878,915 A | | 11/1989 | Brantigan |
| 4,961,740 A | | 10/1990 | Ray et al. |
| 5,015,247 A | | 5/1991 | Michelson |
| 5,059,193 A | | 10/1991 | Kuslich |
| 5,192,327 A | | 3/1993 | Brantigan |
| 5,290,312 A | * | 3/1994 | Kojimoto et al. ............. 623/17 |
| 5,390,683 A | | 2/1995 | Pisharodi |
| 5,405,391 A | * | 4/1995 | Hednerson et al. ........... 623/17 |
| 5,425,772 A | | 6/1995 | Brantigan |
| 5,489,308 A | | 2/1996 | Kuslich et al. |
| 5,653,762 A | | 8/1997 | Pisharodi |
| 5,653,763 A | * | 8/1997 | Errico et al. .................. 623/17 |
| 5,658,336 A | | 8/1997 | Pisharodi |
| 5,693,100 A | | 12/1997 | Pisharodi |
| 5,723,013 A | | 3/1998 | Jeanson et al. |
| 5,749,916 A | | 5/1998 | Richelsoph |
| 5,776,199 A | | 7/1998 | Michelson |
| 5,865,847 A | | 2/1999 | Kohrs et al. |
| 5,865,848 A | * | 2/1999 | Baker ........................... 623/17 |
| 5,980,522 A | | 11/1999 | Koros et al. |
| 6,129,763 A | | 10/2000 | Chauvin et al. |
| 6,174,334 B1 | * | 1/2001 | Suddaby .................. 623/17.11 |
| 6,183,517 B1 | | 2/2001 | Suddaby |
| 6,224,631 B1 | | 5/2001 | Kohrs |

FOREIGN PATENT DOCUMENTS

| | | |
|---|---|---|
| DE | 298 06 830 U1 | 7/1998 |
| EP | 0 260 044 A1 | 3/1988 |
| EP | 0 664 994 A1 | 8/1995 |
| EP | 0 832 622 A2 | 4/1998 |
| EP | 0 767 636 B1 | 1/1999 |
| FR | 2 734 148 | 11/1996 |
| WO | WO 98/46173 | 10/1998 |
| WO | WO 00/35389 | 6/2000 |
| WO | Wo 00/56513 | 9/2000 |

* cited by examiner

Primary Examiner—Corrine McDermott
Assistant Examiner—Alvin Stewart
(74) Attorney, Agent, or Firm—Merchant & Gould P.C.

(57) ABSTRACT

The present invention is directed to expandable bone fusion devices and methods of use. In general, a fusion device according to the invention includes a first member and a second member which can be deployed and locked into an expanded configuration to stabilize the adjacent bone during fusion of the bone.

16 Claims, 4 Drawing Sheets

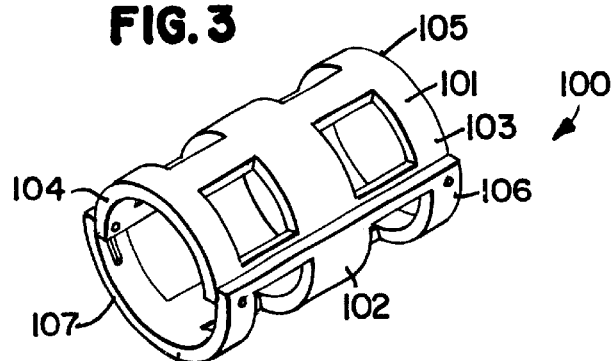
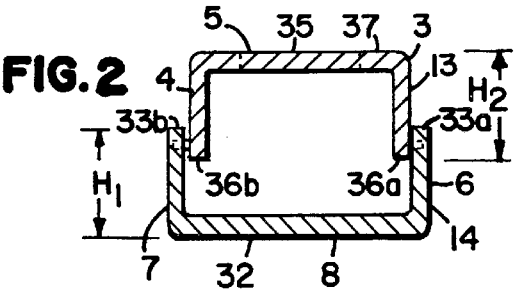
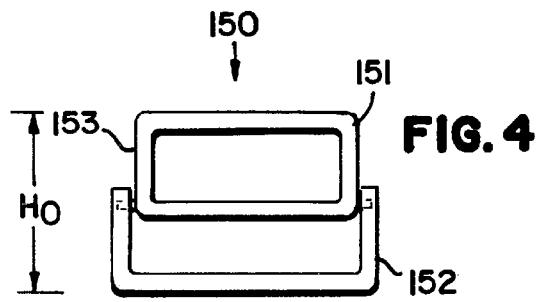
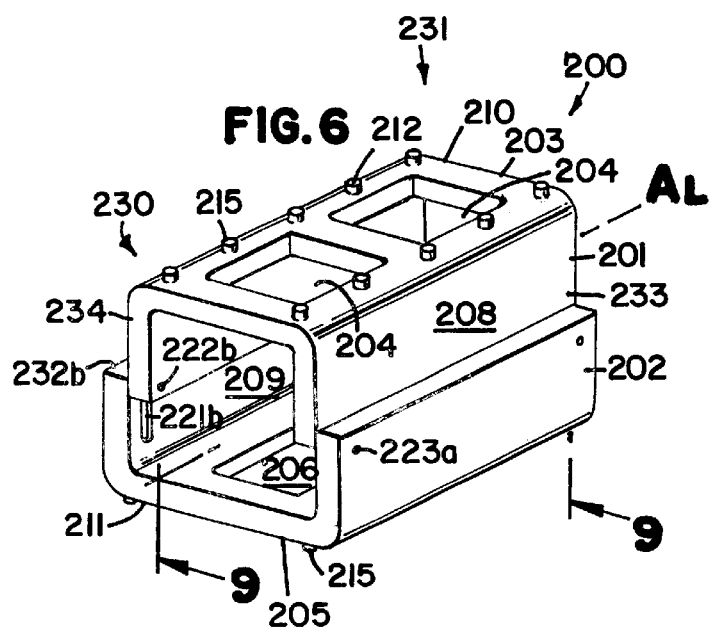

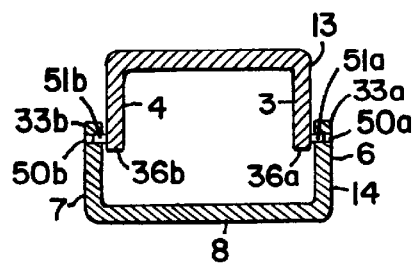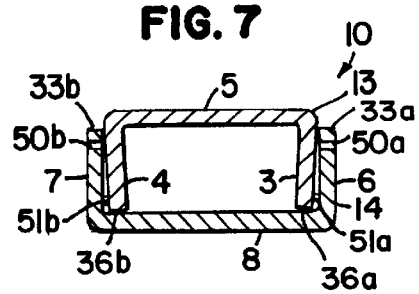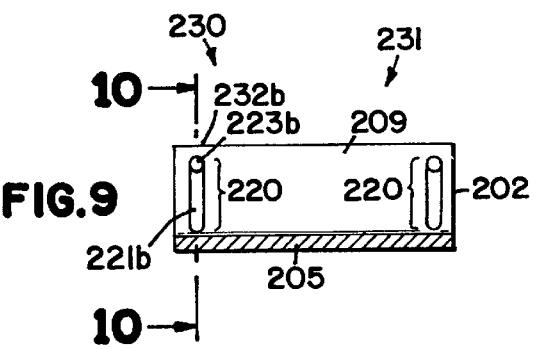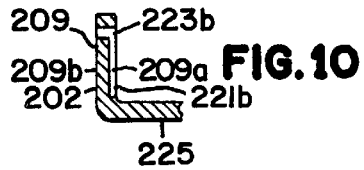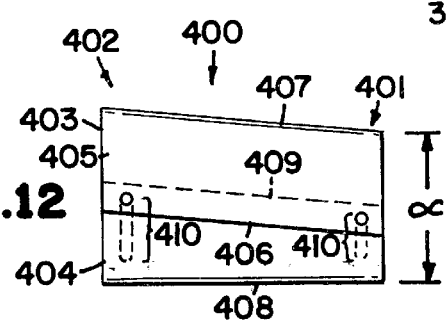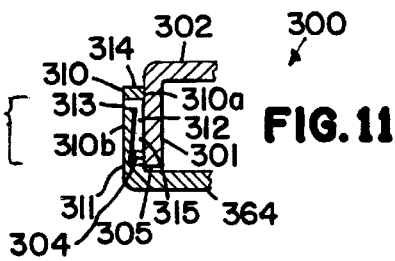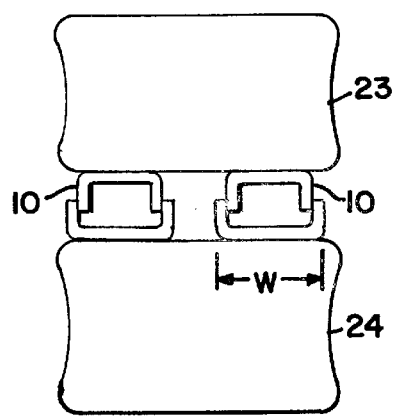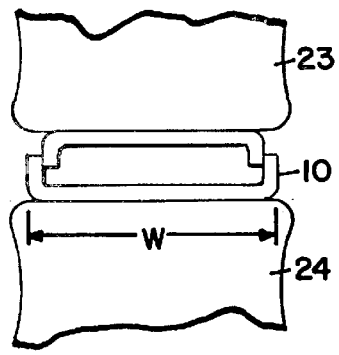

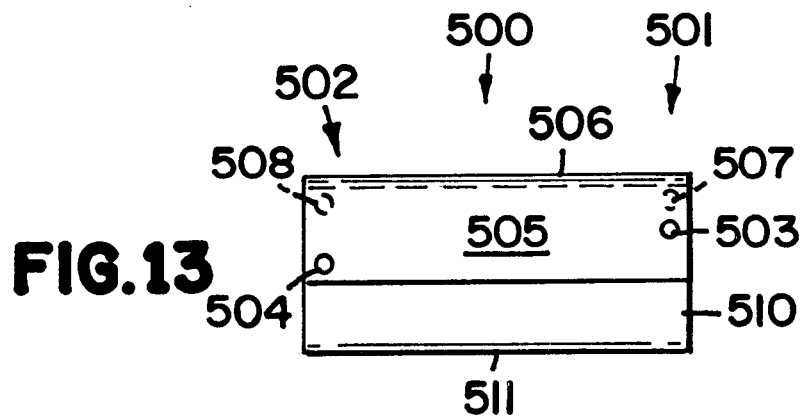
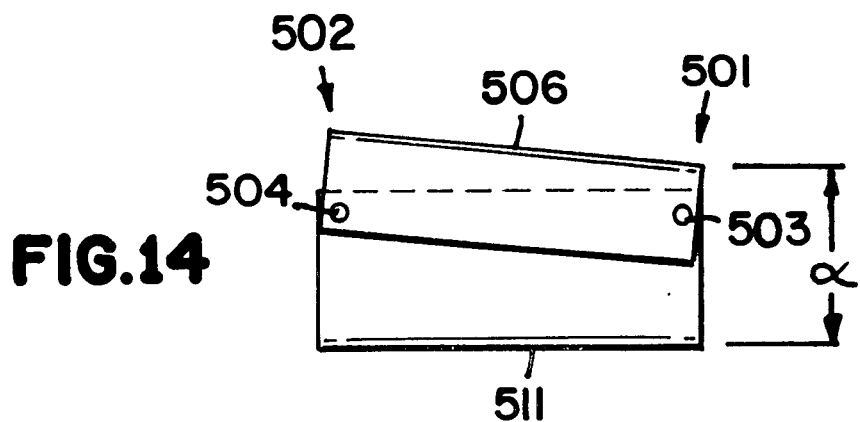

EXPANDABLE FUSION DEVICE AND METHOD

FIELD OF THE INVENTION

The present invention pertains to devices and methods for facilitating bone fusion. The devices and methods disclosed can be used for fusion of joints. The invention is particularly advantageous for fusion of intervertebral joints.

BACKGROUND OF THE INVENTION

Chronic back problems cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Stabilization and/or arthrodesis of the intervertebral joint can reduce the pain associated with movement of an intervertebral joint having diseased disc material. Generally, fusion techniques involve removal of the diseased disc and packing the void area with a suitable matrix for facilitating a bony union between the opposing vertebral bodies.

Surgical devices for facilitating interbody fusion have also been developed. These devices typically provide for maintaining appropriate intervertebral spacing and stabilization of the vertebrae during the fusion process. Examples of such devices are disclosed in, for example, U.S. Pat. Nos. 5,458,638, 5,489,307, 5,055,104, 5,026,373, 5,015,247, 4,961,740, 4,743,256 and 4,501,269, the entire disclosures of which are incorporated herein by reference.

Present methods for implanting a fusion device often require that the vertebrae be distracted to restore a diseased disc space to its normal height prior to implanting a fusion device In addition, the disc space is typically prepared for receiving an implant by drilling and tapping a bore of appropriate size for receiving the implant. Hence, current methods used for inserting presently available fusion implants require several steps and specialized instrumentation to prepare the implant site.

The time required to perform the steps for preparing the implant site prolongs the duration of the surgical procedure and thus, increases the duration of time that the patient is under general anesthesia. Also, the instrumentation used may require making a substantial skin incision. Furthermore, the steps used to distract and prepare the implant site increase the chance for trauma to neural, vascular and other tissues in the vicinity of the implant site.

Accordingly, there is a continuing need for improved intervertebral stabilizing devices and methods. The present invention is directed to addressing these needs.

SUMMARY OF THE INVENTION

The present invention is directed to an implant and methods for facilitating fusion of bone. The invention can be advantageously used in the stabilization and fusion of a joint, particularly an intervertebral joint. The invention helps to reduce the steps necessary for preparing the implant site and the time required for performing the overall implantation procedure. The invention also reduces the chance of injury to issues near the surgical site.

It will be appreciated that throughout the specification, guidance may be provided through lists of examples. In each instance, the recited list serves only as a representative group. It is not meant, however, that the lists are exclusive.

An intervertebral fusion device according to the invention can have an expanded and a non-expanded configuration. The fusion devices have an internal surface, an external surface, a leading end and a trailing end. A portion of the external surfaces include an engagement arrangement to reduce the likelihood of movement or expulsion of the fusion device once implanted within the intervertebral space. The interior of the fusion devices can be packed with a bone support matrix to facilitate fusion between opposing bone surfaces.

The fusion devices each include an external member and an internal member. A portion of both the external and internal members can have a U-shaped configuration. The external member includes an external base and a first and second external side wall spaced apart by a width of the external base. The internal member also includes an internal base and a first and second internal wall spaced at an appropriate distance to permit the first and second internal walls to fit within the first and second external walls.

The fusion devices also include a locking arrangement. In general, a locking arrangement includes a pair of pins which interdigitate with a pair of apertures. In one embodiment, a first pin can project from the first internal wall and a second pin can project from the second internal wall. The first and second pins lock by interdigitating with a first and second aperture located on the first and second external walls respectively.

In an alternative embodiment, a first pin can project from the first external wall and the second pin can project from the second external wall. According to this embodiment, when locked in the deployed position, the first pin interdigitates with a first aperture located on the first internal wall and the second pin interdigitates with a second aperture located on the second internal wall. The invention describes various permutations of the relative positioning of the pins and the apertures to permit locking the fusion device in various expanded configurations. In some embodiments, the walls in which the apertures are located also include a groove to guide the pins into the aperture.

The invention also provides methods for implanting the fusion devices disclosed. In general, after preparation of the joint space, the leading end of the fusion device is inserted into the joint space and deployed into the expanded configuration. In addition to other advantages, the method disclosed can provide for reduced surgery time and reduced chance of trauma to tissues surrounding the joint space being fused.

BRIEF DESCRIPTION OF THE DRAWINGS

FIG. 2 is a cross-sectional view of an alternative embodiment of a fusion device according to the invention in an expanded configuration.

FIG. 3 is a perspective view of an alternative embodiment of a fusion device according to the invention in an expanded configuration;

FIG. 4 is an end-on view of an alternative embodiment of a fusion device according to the invention;

FIG. 6 is a perspective view of an alternative embodiment of a fusion device according to the invention;

FIG. 7 is a transverse section view through line 7—7 of the fusion device of FIG. 1 in a non-expanded configuration;

FIG. 8 is a section view through line 7—7 of the fusion device of FIG. 1 in an expanded configuration;

FIG. 9 is a section view through line 9—9 of the external member of FIG. 6;

FIG. 10 is a section view through line 10—10 of FIG. 9;

FIG. 11 is a section view taken from the same position as FIG. 10 in an alternative embodiment of a locking arrangement according to the invention;

FIG. 12 is a side view of one embodiment of a lordotic fusion device according to the invention;

FIG. 13 is a side view of an alternative embodiment of a lordotic fusion device of the invention in a non-expanded configuration;

FIG. 14 is a side view of the lordotic fusion device of FIG. 13 in an expanded configuration;

FIG. 15 is an anterior view of adjacent vertebrae with two fusion devices according to the invention inserted therebetween; and FIG. 16 is an anterior view of adjacent vertebrae with a single fusion device according to the invention inserted therebetween.

DETAILED DESCRIPTION OF THE INVENTION

Figure 1:
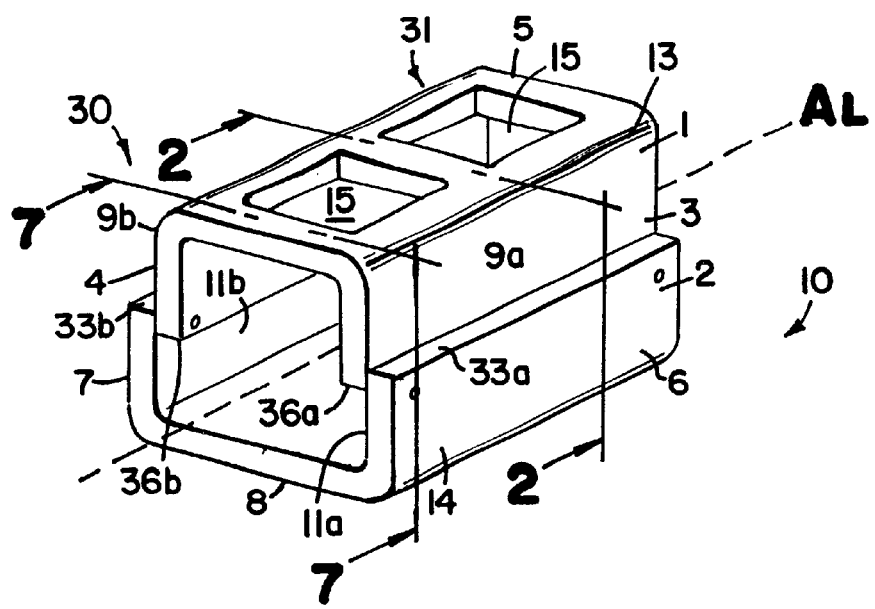
FIG. 1 is a perspective view of a fusion device according to the invention in an expanded configuration.

The present invention is directed to an implant and methods for facilitating stabilization or fusion of bones. The invention can be advantageously used in the stabilization and fusion of a joint, particularly an intervertebral joint. Thus, the invention will be described with reference to stabilization and fusion of adjacent lumbar vertebrae. It will be appreciated, however, that the devices and methods disclosed are applicable for use with all types of joints (e.g., ankle, intervertebral, interdigital, etc.) and in all regions (e.g., arms, legs, spine, etc.) of a human or animal body. In the spinal column, the devices and methods disclosed can be used at all intervertebral joints, including those in the cervical, thoracic and lumbar region.

In use, a fusion device of the invention can be inserted into a joint space in a close packed configuration and then deployed into an expanded configuration and locked in the expanded configuration to stabilize the joint space. In preferred embodiments, the devices can include openings for bone growth through the device to fuse the joint.

According to the invention a fusion device (implant) includes a body having an exterior region and an interior region. Generally portions of the exterior region engage the bones adjacent the joint space to be fused. When inserted between the bones and deployed, the device stabilizes the joint by exerting an outward force against the bones which counters the contracting (inward) force of the soft tissue structures surrounding the joint. The interior region of the fusion device defines an interior space or chamber which can be filled with a bone growth matrix to facilitate bone growth across the fusion site.

The body of a fusion device comprises, at least, a first and second member, one of which nests inside the other in a close packed configuration when the fusion device is in the non-deployed state. A portion of each member includes a generally U-shaped configuration in cross-section, regardless if the member is open or closed (i.e., tubular). The U shape can be in the form of a rectangle, circular, oval, etc.

Each member includes opposing side walls spaced apart by a base. The width of the bases of each member determines the overall width of the device. The height of the walls and position of the locking arrangement determines the overall height and angulation of the device when in the deployed configuration.

Once inserted into a joint space, the implant can be deployed and the members locked into an expanded configuration. A locking arrangement for locking the device preferably includes a locking pin and locking pin hole for receiving the locking pin. The transverse cross sectional configuration of the locking pin can be any shape, including, circular, square, rectangular, polygonal, etc. The longitudinal cross-sectional configuration of the pin can be parallel, conical, etc. The cross sectional configuration of the locking pin hole is selected to cooperatively receive the locking pin.

In use, the implants are typically inserted into a disc space in a compact (non-expanded) configuration between adjacent vertebrae. Once inserted into the joint space the implant can be deployed and locked into an expanded configuration to form a desired disc space height between the vertebrae. As used herein, a "desired" disc space height refers to the distance between the vertebrae which is determined to be appropriate for the particular condition of the patient. Thus, depending on the condition, the desired height may be that of the normal disc space when in a non-diseased condition or the disc space may be greater than the normal disc space height or less than normal. An example of the range of the overall height dimension of an implant of the invention for intervertebral use when in the contracted configuration can be about 2 to 10 mm. An example of the range of the overall height dimension of the same implant when in the expanded configuration is about 4 to 20 mm.

In general, the overall height of the fusion devices can be varied by varying the height of each member of the body. In addition, in some embodiments, a device of the invention can include a taper to provide a desired degree of angulation between the adjacent bones. In the case of an intervertebral joint, the angle provided can be about 0° to 25°.

One or more fusion devices can be implanted in a single joint space. In the case of an intervertebral joint, the number of devices and the length and width dimensions of the devices can preferably be selected such that the device or devices fit and operate within the margins of the adjacent vertebral bodies. Examples of ranges of lengths and widths of devices of the invention are about 20 to 50 mm long and 5 to 50 mm wide.

The fusion devices have a "leading end" and a "trailing end." The terms "leading end" and "trailing end" are relative terms indicating that in typical use, the leading end of the implant is inserted into the joint space followed by the trailing end. The device can also be referred to in terms of a "distal end" and a "proximal end" based on the orientation of the implant relative to the surgeon. The fusion devices can be inserted into an intervertebral disc space through most known approaches including, anterior, posterior, lateral, etc.

A portion of the exterior region of each of the members can include a biological surface or a biocompatible material having surfaces which coaptate with the surfaces of bone or bone end plates surrounding the joint space. Suitable coaptating surfaces are typically contoured and include, for example, a porous bone ingrowth surface, spikes, knurls, ridges, threads, or other similar arrangement to facilitate stabilization of the implant in the joint space. In the case of a device having a circular cross section, helical threads can be provided for inserting the implant into a tapped or non-tapped disc space.

Suitable materials for manufacturing a fusion device of the invention include metals such as titanium, stainless steel, cobalt-chromium, etc.; alloys including titanium alloys and non-titanium alloys; superelastic materials such as nitinol; plastics and plastic composites; carbon graphite; ceramic; etc. In some embodiments, the first and/or second member may be deflected when in the close packed position or the member may be deflected when being deployed into the expanded configuration. In these embodiments, the member deflected preferably has elastic properties permitting deflection of the member within its material limits without significantly affecting the structural integrity of the member.

According to the method of the invention, in one embodiment, prior to insertion, a discectomy can be performed, and, preferably, the annular ligament preserved. The endplates of the bone can be scraped, curretted or similar procedure performed to create an exposed end surface for facilitating bone growth across the fusion site. Then, with the device in the close packed configuration, the leading end can be inserted into the disc space followed by the trailing end. In some circumstances, it may be advantageous to distract the adjacent vertebrae prior to insertion of a fusion device. Such distraction can provide for easier removal of disc material and/or greater exposure to facilitate preparation of the end plates. Distraction can also provide greater accuracy in determining the appropriate size fusion device to implanted.

Once inserted at the appropriate location the device can be deployed. If more than one implant is used at a particular joint space, each implant can be positioned within the joint space prior to deployment. Alternatively, individual implants can be inserted and deployed prior to insertion of a subsequent implant at the same joint space.

When a cylindrical fusion device is used, it may be advantageous to first drill a bore into the disc space of a size sufficient for receiving the device prior to insertion. In some embodiments, the bore may also be tapped for guiding threads which may be present on the surface of the device.

The fusion devices can be deployed into the expanded configuration and locked in this configuration using, for example, a reverse plier, spreader, retractor, etc. Once deployed, the interior chamber of the fusion device and/or void areas surrounding the device(s) can be packed with a bone support matrix to facilitate bone growth into the joint space. As used herein, a "bone support matrix" is a material that facilitates new bone growth between the opposing vertebral bodies. Suitable bone support matrices can be resorbable or nonresorbable and osteoconductive or osteoinductive. Examples of suitable matrices according to the invention include synthetic materials, such as Healous™, available from Orquest, Mountain View, Calif.; NeOsteo™, available from Sulzer Orthopedic Biologics, Denver, Co.; or any of a variety of bone morphogenic proteins (BMPs). Suitable bone support matrices also include heterologous (xenograft), homologous (allograft), or autologous (autograft) bone and derivatives thereof. Preferably, the bone support matrix is radiolucent on x-rays.

The fusion devices of the invention can be included in a kit comprising a plurality of incrementally sized implants which can be selected by the clinician based on the size needed for a particular patient. In other embodiments kits can include instrumentation for performing an implant procedure with or without a plurality of incrementally sized implants.

The fusion devices of the invention will now be further described by reference to the following illustrated embodiments. The illustrated embodiments are not intended to limit the scope of the invention, but rather, are provided to facilitate understanding of the devices and methods within the principles of the invention.

DETAILED DESCRIPTION OF THE ILLUSTRATED EMBODIMENTS

With reference to the several drawing figures, a description of embodiments of an expandable fusion device according to the present invention will now be provided. The following discussion describes a fusion device of the invention with reference to implanting the device between adjacent lumbar vertebrae. However, this description is for explanatory purposes only. As stated above, the devices disclosed herein can be used at other joints or other spinal locations to facilitate bone fusion.

FIG. 1 is a perspective view of one embodiment of a fusion device 10 according to the invention in an expanded configuration. Fusion device 10 includes a first member 1 and a second member 2. As illustrated, first member 1 includes a first side wall 3 and a second side wall 4 spaced apart by a base 5. Second member 2 also includes a first side wall 6 and a second side wall 7 spaced apart by base 8. In the illustrated embodiment, the exterior surface 9a of first side wall 3 and the exterior surface 9b of second side wall 4 of first member 1 fit within the interior surfaces 11a and 11b of first side wall 6 and second side wall 7, respectively, of second member 2. Thus, because first side wall 6 and second side wall 7 of second member 2 are "external" to first side wall 3 and second side wall 4 of first member 1, second member 2 can also be referred to as external member 14 and first member 1 can be referred to as internal member 13 of fusion device 10. In this embodiment, the leading end 30 of fusion device 10 is identical to trailing end 31.

FIG. 2 is a transverse cross-section view through line 2—2 of FIG. 1. As illustrated, the cross-section of internal member 13 and external member 14 have a "U"-shaped appearance. The U-shape of fusion device 10 in FIG. 1 is substantially rectangular. That is, for example, side walls 3 and 4 each form a right angle with base 5. However, the shape of a fusion device 10 is not limited to a rectangular cross section, other shape fusion devices are included within the scope of the invention. For example, fusion device 100, illustrated in FIG. 3, has a substantially circular transverse cross section appearance. According to the embodiment of FIG. 3, first member 101 includes side walls 103 and 104 which meet at apex 105. Second member 102 includes side walls 106 and 107 which meet at apex 108. Fusion device 100 can be implanted within a cylindrical bore prepared between adjacent vertebrae as will be described below. When implanted, fusion device 100 will contact the end plates of opposing vertebrae at the apexes (105, 108) and along a portion of each of the side walls (103, 104, 106 and 107).

FIG. 4 is an end-on view of another embodiment of a fusion device 150 which comprises an internal member 151 and an external member 152. In this embodiment, internal member 151 is closed, or has a tubular configuration 153.

Figure 5:
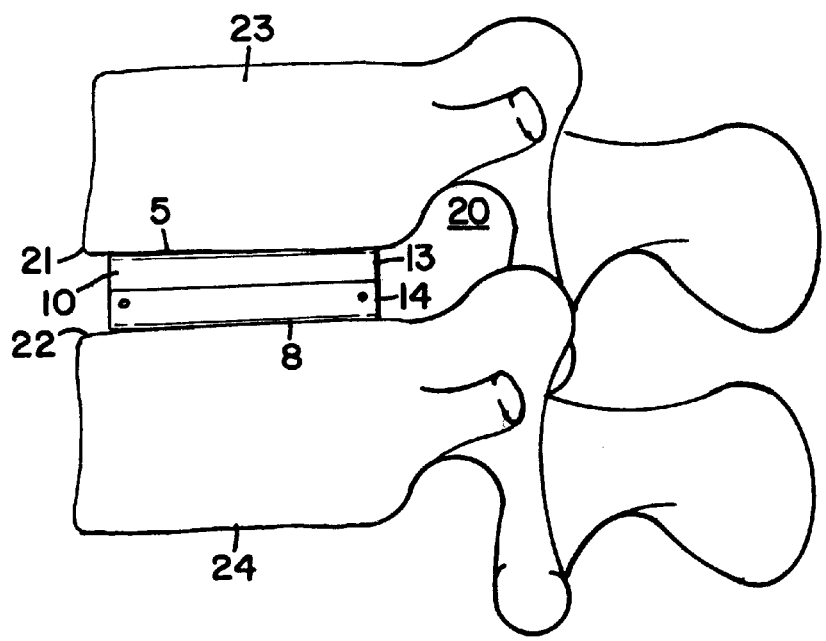
FIG. 5 is a lateral view of the fusion device of FIG. 1 positioned between adjacent vertebrae.

FIG. 5 is a lateral view of a fusion device 10 inserted between opposing vertebrae. In use, fusion device 10 is inserted in the disc space 20 between the end plates 21 and 22 of opposing vertebrae 23 and 24. In FIG. 5, fusion device 10 is inserted into disc space 20 in the orientation illustrated in FIG. 1. Thus, base 5 of internal member 13 is positioned to contact end plate 21 and base 8 of external member 14 is positioned to contact end plate 22. However, it will be appreciated that fusion device 10 could also be inserted into a disc space 20 rotated 180° around long axis $A_L$, regardless of the approach used for insertion.

As illustrated in FIG. 1, the bases 5 and 8 which contact the end plates of the adjacent vertebrae can include openings 15 as illustrated for base 5 or no openings as illustrated for base 8. Providing openings 15 in base 5 and 8 advantageously promotes greater continuity of new bone growth within fusion device 10.

Referring again to FIGS. 1 and 2, the leading end 30 and trailing end 31 of fusion device 10 are identical. Thus, the height ($H_1$) of side walls 6 and 7 of external member 14 measured from the exterior base 32 of base 8 to either of external edges 33a or 33b, is identical at the leading end and trailing end 31 of the device. Likewise, the height ($H_2$) of the side walls of internal member 13, measured from the exterior base 35 of base 5 to either internal edge 36a or 36b, is the same at the leading and trailing end. In some embodiments, the overall height ($H_0$) measured from the exterior 35 of base 5 to the exterior 32 of base 8, can be different due to: a difference in the height ($H_1$) of internal side wall (3, 4) at the leading end and trailing end, a difference in the height ($H_2$) of external side wall (6, 7) at the leading and trailing end; or a difference in the position of the components of the locking arrangement (discussed below).

FIG. 6 illustrates an alternative embodiment of a fusion device 200 including internal member 201 and external member 202. In this embodiment, base 203 of internal member 201 includes a plurality of openings 204. In addition, base 205 of external member 202 also includes openings 206. In alternative embodiments, the bases can include none, one, two, three or more openings. In addition, the exterior surfaces 210 and 211 of bases 203 and 205, respectively, include an engagement arrangement 212 to facilitate engagement of fusion device 200 with the end plates of the vertebrae. Use of an engagement arrangement 212 reduces the likelihood of migration or expulsion of the device after implantation. In FIG. 6, engagement arrangement 212 includes a plurality of spikes 215 along the exterior base surfaces 210 and 211. Alternative engagement arrangements 212 can also be used including, for example, porous coated exterior ingrowth surfaces, knurls, ridges, threads, etc.

The operation of a fusion device according to the invention will now be described. FIG. 7 is a transverse cross-section view through fusion device 10 at line 7—7 of FIG. 1 in a non-expanded configuration. As illustrated, apertures 50a and 50b extend through side walls 6 and 7, near the external edges 33a and 33b of external member 14. Apertures 50a and 50b are sized for receiving pins 51a and 51b positioned near the internal ends 36a and 36b, respectively, of side walls 3 and 4 of internal member 13. Thus, when in the non-expanded position, internal ends 36a and 36b are positioned near or against base 8. Also, when fusion device 10 is in the non-deployed configuration, side walls 3 and 4 of internal member 13 are deflected towards one another within the elastic limits of the material of the internal member 13.

After insertion into the intervertebral space, fusion device 10 can be deployed into the expanded position using a reverse plier (e.g., Inge Retractor, KMedic), spreader or retractor to force bases 5 and 8 away from one another into the deployed configuration in FIG. 8. As illustrated, pins 51a and 51b interdigitate with apertures 50a and 50b, respectively, to lock fusion device 10 in the expanded position.

Referring to FIGS. 6, 9 and 10, fusion device 200 includes an alternative embodiment of a locking arrangement 220 for locking fusion device 200 in the deployed configuration. According to this embodiment, external member 202 includes grooves 221a (not visible) and 221b along the interior surface of side walls 208 and 209, respectively, for guiding pins 222a (not visible) and 222b into apertures 223a and 223b respectively.

FIG. 9 is a longitudinal section view through line 9—9 of external member 202. As illustrated, a locking arrangement 220 is present at the leading end 230 and trailing end 231 of fusion device 200. Focusing on the leading end 230, aperture 223b is positioned near the external edge 232b of external member 202. Groove 221b extends from near base 205 to aperture 223b. FIG. 10 is a section view through line 10—10 of FIG. 9 showing that groove 221b extends from near base 205 to aperture 223b. In this embodiment, when in the non-deployed state, side walls 233 and 234 of internal member 201 are deflected towards the longitudinal axis $A_L$ of fusion device 200.

It will be appreciated that while the embodiment of fusion device 200 of FIGS. 6, 9 and 10 illustrate that the aperture 223b traverses the thickness of wall 209 from interior 209a to exterior 209b, the depth of apertures such as 223b need not traverse the entire wall thickness, but need only be sufficiently deep to provide the locking function of the locking arrangement.

Referring now to FIG. 11, an alternative embodiment of a locking arrangement 320 is illustrated for fusion device 300. FIG. 11 is a view from the same location of a fusion device as that of FIG. 10. In this embodiment, side wall 301 of internal member 302 of fusion device 300 includes a pin 304 near the internal edge 305 of side wall 301. Side wall 310 of external member 311 includes a groove 312 leading to aperture 313 near the external edge 314. However, according to this embodiment, groove 312 is ramped 315. That is, groove 312 extends deeper into the thickness of wall 310 (from the interior surface 310a to the exterior surface 310b) near base 314 than it does near aperture 313. Thus, in one preferred form of this embodiment, side wall 301 is only deflected inwardly towards the opposing internal wall during deployment as external member 311 and internal member 302 are being separated and pin 304 is moving from a position near base 311 to aperture 313.

While the foregoing embodiments describe a fusion device having pins projecting from the internal wall and apertures (and grooves) in the external wall, the pins could also project inwardly from the external walls to interdigitate with apertures in the internal walls. Also, while the foregoing discussion of fusion devices describes deflection of internal walls, depending on the material of the device, some elastic deflection of the walls of both the internal and external members can occur without substantially affecting the function of the devices of the invention.

In another embodiment, a fusion device according to the invention can be configured for creating and maintaining a desired degree of lordosis between the adjacent vertebrae. FIG. 12 is a side view of one embodiment of such a lordotic fusion device. As illustrated, device 400 includes a divergent angle α tapering from leading end 401 to trailing end 402. In this embodiment, external member 403 is positioned above internal member 404. Side wall 405 of external member 403 includes parallel surfaces along external edge 406 and base 407. In contrast, base 408 of internal member 404 is not parallel with internal edge 409. Locking arrangements 410 can be in the form of any of the embodiments described above.

FIG. 13 illustrates a side view of an alternative embodiment of a lordotic fusion device 500. According to this embodiment, when in the non-expanded configuration, there is no taper from leading end 501 to trailing end 502 when fusion device 500 is in non-expanded configuration. However, as shown in FIG. 13, apertures 503 and 504 of external member 505 are not positioned an equal distance from base 506. Rather, aperture 503 is positioned closer to base 506 than is aperture 504. Pins 507 and 508 (hatches) of internal member 510 are located the same distance from base 511. Thus, when deployed, as illustrated in FIG. 14, fusion device 500 can be locked into position to a configuration providing a lordotic taper of angle α. Various relative positions of apertures 503 and 504 can be used to create different devices having different degrees of angulation. Alternatively, the aperture positions can remain fixed and the position of pins 507 and 508 can be varied to provide a lordotic fusion device similar to that described for fusion device 500.

In use, a single fusion device may be inserted into the disc space between opposing vertebrae. Alternatively, two fusion devices may be implanted parallel to one another as described for non-expandable fusion devices as disclosed in, for example, U.S. Pat. No. 5,489,307, the entire disclosure of which is incorporated herein by reference.

According to the method of the invention, the disc space to be fused can be identified, and a surgical approach to the disc made, using methods known in the art. Once the disc space is exposed, a discectomy can be performed. A portion of the end plates can be removed to create bleeding edges to facilitate fusion. If an anterior approach is used for implanting two fusion devices, a first fusion device is inserted between the adjacent vertebrae on a first side of the mid-line of the disc space. The first fusion device can be deployed once in position. The second fusion device can then be placed on the second side of the midline and subsequently deployed. Alternatively, the first and second fusion devices may first be placed into the intervertebral disc space and subsequently deployed. If the tissues surrounding the joint prevent full deployment of a selected fusion device for the locking arrangement to lock, an alternative fusion device having a shorter overall height Ho may need to be used. Alternatively, a greater depth of the bone ends may be removed to accommodate the overall height ($H_0$) of the originally selected fusion device.

FIG. 15 is a diagrammatic illustration of an anterior view two fusion devices 10 according to the invention in an expanded configuration between adjacent vertebrae 23 and 24. According to this embodiment, preferably, the width (W) of each fusion device 10 is selected such that when in the disc space, the fusion devices are completely within the margins of vertebrae 23 and 24.

FIG. 16 is a diagrammatic illustration of an anterior view of a single fusion device 10 in the disc space between adjacent vertebrae 23 and 24. According to this embodiment, the width (W) of fusion device 10 is of sufficient size to provide stability across a major portion of the articular surfaces of vertebrae 23 and 24, preferably without extending beyond the margins of the vertebrae.

As stated previously, the fusion devices disclosed herein can be implanted through approaches known in the art, including, anterior, posterior, lateral, etc. Various size implants will be available ranging in size from 5 to 50 mm in width. Because a fusion device(s) of the invention can assume a close packed configuration, the devices of the invention require a smaller skin incision and reduce the likelihood of trauma to neural and/or vascular structures during surgical implantation. In addition, the time required for performing an implant procedure can be reduced because distraction procedures prior to implementation are optional.

If a fusion device having a circular cross-section as illustrated in FIG. 3 is used, a cylindrical bore will likely need to be created between adjacent vertebrae at the affected disc space. Methods for creating cylindrical bores are known. However, in contrast to some methods for creating a cylindrical bore between opposing vertebrae such as disclosed in U.S. Pat. No. 5,489,307, no distraction is required prior to preparing the bore according to the methods of the present invention.

After the fusion devices are inserted, the intervertebral space not occupied by the fusion devices and the interior of the body of the fusion devices may be filled with a bone support matrix as described above.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

What I claim is:

1. An intervertebral implant having an expanded and non-expanded configuration, wherein the implant has a longitudinal axis extending from a leading end of the implant to a trailing end of the implant and a midline between the leading end and trailing end positioned transverse to the longitudinal axis of the implant, the implant comprising:

an external member including a first external wall spaced apart from a second external wall;

an internal member including:
a first internal wall spaced apart from a second internal wall such that the first and second internal walls are disposed within the first and second external walls, wherein when in the non-expanded configuration the first and second internal walls are deflected towards one another;

a locking arrangement comprising:
a first locking structure proximate to the midline of the implant and disposed between one of the first external wall and first internal wall or the second external wall and second internal wall; and
a second locking structure positioned distal to the midline of the implant and disposed between one of the first external wall and first internal wall or the second external wall and second internal wall, wherein the first locking structure is spaced apart from the second locking structure.

2. An intervertebral implant having an expanded and non-expanded configuration and comprising:
an external member including:
a leading end and a trailing end,
an external base;
a first external wall and a second external wall spaced apart by a width of the external base, each of the first and second external walls having an external base end nearest the external base and an external edge away from the external base;
an internal member including:
a leading end and a trailing end,
an internal base;
a first internal wall and a second internal wall having a spacing therebetween for the first and second internal walls to fit within the first and second external walls, each of the first and second internal walls having an
internal base end nearest the internal base and an
internal edge away from the internal base, wherein
when in the non-expanded configuration the first and
second internal walls are deflected towards one
another;

a locking arrangement, comprising:
a first pin projecting from one of the first internal wall
or the first external wall, proximate the leading end;
a first aperture in one of the first internal wall or the first
external wall, proximate the leading end wherein the
first aperture is configured to receive the first pin
when the implant is in an expanded configuration;
a first groove extending from the first aperture towards
the base end of the first internal wall or the first
external wall;
a second pin projecting from one of the second internal
wall or the second external wall, proximate the
leading end;
a second aperture in one of the second internal wall or
the second external wall, proximate the leading end
wherein the second aperture is configured to receive
the second pin when the implant is in an expanded
configuration; and
a second groove extending from the second aperture
towards the base end of the second internal wall or the
second external wall.

3. The intervertebral implant according to claim 1, wherein the first locking structure includes a first pin projecting from one of the first internal wall or first external wall and a first aperture in a first opposing wall configured to receive the first pin when the implant is in the expanded configuration; and the second locking structure includes a second pin projecting from one of the second internal wall or second external wall and a second aperture in a second opposing wall configured to receive the second pin when the implant is in the expanded configuration.

4. The intervertebral implant according to claim 1 or 2, wherein the external member is U-shaped.

5. The intervertebral implant according to claim 1 or 2, wherein the internal member is U-shaped.

6. The intervertebral implant according to claim 1 or 2, wherein the internal member is tubular.

7. The intervertebral implant according to claim 1 or 2, wherein the first and second members each have a circular cross section.

8. The intervertebral implant according to claim 1 or 2, wherein the internal and external members each have a rectangular cross section.

9. The intervertebral implant according to claim 1 or 2, wherein the internal member and external member each include at least one opening.

10. The intervertebral implant according to claim 1 or 2, wherein at least one of an exterior surface of the external member and an exterior surface of the internal member include an engagement arrangement for engaging end plate of adjacent vertebrae.

11. The intervertebral implant according to claim 1 or 2, wherein the engagement member comprises a spike.

12. An intervertebral implant having an expanded and non-expanded configuration and comprising:
an external member including:
a leading end and a trailing end,
an external base;
a first external wall and a second external wall spaced apart by a width of the external base, each of the first and second external walls having an external base end nearest the external base and an external edge away from the external base; and
an internal member including:
a leading end and a trailing end,
an internal base; and
a first internal wall and a second internal wall having a spacing therebetween for the first and second internal walls to fit within the first and second external walls, each of the first and second internal walls having an internal base end nearest the internal base and an internal edge away from the internal base; wherein when in the non-expanded configuration the first and second internal walls are deflected towards one another.

13. An intervertebral implant according to claim 12 wherein a trailing height of the first and second internal walls, measured from the internal base to the internal edge at the trailing end of the first and second internal walls, is greater than a leading height of the first and second internal walls, measured from the internal base to the internal edge at the leading end of the first and second internal walls.

14. The intervertebral implant according to claim 12, wherein the second locking structure includes a third pin projecting from one of the first internal wall or first external wall and a third aperture in a third opposing wall configured to receive the third pin when the implant is in the expanded configuration; and a fourth pin projecting from one of the second internal wall or second external wall and a fourth aperture in a fourth opposing wall configured to receive the fourth pin when in the expanded configuration.

15. An intervertebral implant having an expanded and non-expanded configuration, wherein the implant has a longitudinal axis extending from a leading end of the axis to a trailing end of the axis with a midline between the leading end and trailing end positioned transverse to the longitudinal axis, the implant comprising
an external member including:
a leading end and a trailing end,
an external base;
a first external wall and a second external wall spaced apart by a width of the external base, each of the first and second external walls having an external base end nearest the external base and an external edge away from the external base;
an internal member including:
a leading end and a trailing end,
an internal base;
a first internal wall and a second internal wall having a spacing therebetween for the first and second internal walls to fit within the first and second external walls, each of the first and second internal walls having an internal base end nearest the internal base and an internal edge away from the internal base;
a first pin projecting from one of the first internal wall or first external wall proximal to the midline of the implant and a first aperture in an opposing wall configured to receive the first pin when the implant is in the expanded configuration;
a second pin projecting from one of the second internal wall or second external wall proximal to the midline of the implant and a second aperture in an opposing wall configured to receive the second pin when the implant is in the expanded configuration;
a third pin projecting from one of the first internal wall or first external wall distal to the midline of the implant and a third aperture in an opposing wall configured to receive the third pin when the implant in the expanded configuration; and a fourth pin projecting from one of the second internal wall or second external wall distal to the midline of the implant-and a fourth aperture in an opposing wall configured to receive the fourth pin when in the expanded configuration;

wherein the third and fourth pins and are spaced apart from the first and second pins and a distance between the external base and the first aperture is less than a distance between the external base and the third aperture.

16. An intervertebral implant according to claim 15 wherein a distance between the internal base and the first pin is less than a distance between the internal base and the third pin.

* * * * *